United States Patent
Qu et al.

(10) Patent No.: US 11,698,298 B2
(45) Date of Patent: Jul. 11, 2023

(54) AUTOMATIC DARKENING FILTER WITH ADAPTIVE PARAMETER ADJUSTMENT AND WORKING METHOD THEREOF

(71) Applicant: CHANGZHOU SHINE SCIENCE & TECHNOLOGY CO., LTD., Changzhou (CN)

(72) Inventors: Jin Qu, Changzhou (CN); Weiren Gao, Changzhou (CN)

(73) Assignee: CHANGZHOU SHINE SCIENCE & TECHNOLOGY CO., LTD., Jiangsu (CN)

( * ) Notice: Subject to any disclaimer, the term of this patent is extended or adjusted under 35 U.S.C. 154(b) by 0 days.

(21) Appl. No.: 17/561,935

(22) Filed: Dec. 25, 2021

(65) Prior Publication Data
US 2022/0378617 A1 Dec. 1, 2022

Related U.S. Application Data

(63) Continuation of application No. PCT/CN2021/099184, filed on Jun. 9, 2021.

(30) Foreign Application Priority Data

Jun. 1, 2021 (CN) .......................... 202110606676.5

(51) Int. Cl.
*G01J 1/42* (2006.01)
*A61F 9/06* (2006.01)
(Continued)

(52) U.S. Cl.
CPC ............ *G01J 1/4204* (2013.01); *A61F 9/067* (2013.01); *G01J 5/00* (2013.01); *G01J 5/0018* (2013.01); *H02S 10/40* (2014.12)

(58) Field of Classification Search
CPC ........... A61F 9/067; G01J 1/4204; G01J 5/00; H02S 10/40; H02S 50/00
See application file for complete search history.

(56) References Cited

U.S. PATENT DOCUMENTS

| 6,483,090 B1 * | 11/2002 | Bae | .................. A61F 9/067 2/8.8 |
| 7,470,880 B2 * | 12/2008 | Huh | .................. G01J 1/26 349/14 |

(Continued)

FOREIGN PATENT DOCUMENTS

| CN | 2168571 Y | 6/1994 |
| CN | 201456997 U | 5/2010 |

(Continued)

*Primary Examiner* — Jennifer D Bennett
(74) *Attorney, Agent, or Firm* — SZDC Law P.C.

(57) ABSTRACT

An automatic darkening filter with adaptive parameter adjustment includes: a welding arc intensity detection unit configured to provide a first signal for determining the welding arc intensity; a solar power supply module configured to provide electric energy for the welding arc intensity detection unit and provide a second signal for determining the ambient light intensity; and a CPU and a light valve, the CPU being configured to calculate a difference between the welding arc intensity and the ambient light intensity based on the first and second signals, and control the scale number of the light valve based on the difference. The automatic darkening filter can realize the automatic adjustment of the scale number, and in the adjustment process, the welding arc intensity signal can be revised based on the ambient light intensity, which can effectively ensure the accuracy of the final determination of the scale number.

7 Claims, 6 Drawing Sheets

(51) Int. Cl.
*H02S 10/40* (2014.01)
*G01J 5/00* (2022.01)

(56) References Cited

U.S. PATENT DOCUMENTS

2009/0094721 A1 4/2009 Becker
2019/0314204 A1 10/2019 Huh

FOREIGN PATENT DOCUMENTS

| CN | 101785725 | A | 7/2010 | | |
| CN | 201993551 | U | 9/2011 | | |
| CN | 110302007 | A | 10/2019 | | |
| CN | 112107418 | A | 12/2020 | | |
| WO | WO-2011127656 | A1 * | 10/2011 | ............. | A61F 9/067 |

* cited by examiner

AUTOMATIC DARKENING FILTER WITH ADAPTIVE PARAMETER ADJUSTMENT AND WORKING METHOD THEREOF

This application is a Continuation Application of PCT/CN2021/099184, filed on Jun. 9, 2021, which claims priority to Chinese Patent Application No. 202110606676.5, filed on Jun. 1, 2021, all of which are incorporated by reference for all purposes as if fully set forth herein.

TECHNICAL FIELD

The present invention relates to the field of welding masks for welders, in particular to an automatic darkening filter with adaptive parameter adjustment and a working method thereof.

BACKGROUND

During welding operation, the welding arc and heat radiation intensity vary depending on the type of welding techniques applied. To cope with different types of welding operations, operators must try to set various parameters of the automatic darkening filter (hereinafter referred to as ADF) for many times prior to welding, so as to achieve the best state that can satisfy the current welding conditions.

Even when the type of welding is determined, different welding workpieces adapt to different welding currents, resulting in different welding arc intensities. Even for the same welding workpiece, different welding locations and different welding angles may result in different welding arc intensities. Therefore, it is necessary for the users to regularly set the various parameters of the ADF to adapt to the current welding arc.

In addition, the mainstream ADFs on the market today all use photoelectric detection technology which employs photoelectric sensors to detect the intensity of the welding arc and control the opening and closing of the light valve, thereby protecting the user's eyes. However, while detecting the welding arc, such photoelectric sensors are susceptible to interference of the ambient light, such as lighting light, sun light, vehicle light, or the like. Such interfering light may affect the accuracy of determining the welding arc by the ADF. When the interfering light is present, the user needs to regularly revise the parameters of the ADF so as to adapt to the current working conditions.

In view of the above-mentioned problems, based on the rich practical experience and professional knowledge engaged in the engineering application of such products for many years, the inventor actively makes research and innovation, and here proposes an automatic darkening filter with adaptive parameter adjustment and a working method thereof.

SUMMARY

The present invention provides an automatic darkening filter with adaptive parameter adjustment, which can effectively solve the problems indicated above. The present invention also provides a working method of an automatic darkening filter with adaptive parameter adjustment, which can achieve the same technical effects.

To this end, the present invention adopts technical solutions detailed below.

There is provided an automatic darkening filter with adaptive parameter adjustment, comprising:

a welding arc intensity detection unit configured to provide a first signal for determining the welding arc intensity;

a solar power supply module configured to provide electric energy for the welding arc intensity detection unit and provide a second signal for determining the ambient light intensity; and a CPU and a light valve, the CPU being configured to calculate a difference between the welding arc intensity and the ambient light intensity based on the first and second signals, and control the scale number of the light valve based on the difference.

The automatic darkening filter with adaptive parameter adjustment further comprises a welding action detection unit configured to provide a third signal for determining whether the welding action is executed, based on which third signal the CPU determines the start time of the difference calculation.

Further, the solar power supply module comprises:

a solar panel configured to generate electricity through ambient light, and generate a varying voltage signal as the second signal based on changes in the ambient light; and a first analog-to-digital (ADC) converter configured to acquire the second signal and convert the same into a second digital signal, and transmit the second digital signal to the CPU.

Further, the welding arc intensity detection unit comprises:

an optical sensor configured to detect an ambient light intensity signal;

a first operational amplifier configured to amplify the ambient light intensity signal as the first signal; and a second ADC converter configured to acquire the first signal and convert the same into a first digital signal, and transmit the first digital signal to the CPU.

Further, the welding action detection unit comprises:

an infrared sensor configured to detect an infrared signal radiated by a welded object; a second operational amplifier configured to amplify the infrared signal as the third signal; and an ACMP comparator configured to acquire and process the third signal, and transmit the processed signal to the CPU.

Further, the CPU is coupled to the second operational amplifier to control an amplification factor of the second operational amplifier.

Further, the automatic darkening filter with adaptive parameter adjustment comprises a RAM memory module and a Flash memory module respectively coupled to the CPU;

the RAM memory module is configured to store the first digital signal and the second digital signal in a one-to-one correspondence;

the Flash memory module is configured to store the correspondence between different scale numbers and different arc intensities; and the CPU is configured to obtain the arc intensity through the difference between the first digital signal and the second digital signal, and obtain the desired scale number through the correspondence.

Further, a timer module is also provided between the CPU and the light valve, which is configured to set the delay time for the light valve to change from black state to standby light state.

There is also provided a working method of the automatic darkening filter with adaptive parameter adjustment, comprising the steps of:

detecting the welding arc intensity to obtain a first signal for determining the welding arc intensity;

generating electricity through the ambient light and using a voltage signal as a second signal for determining the ambient light intensity in the welding site; and calculating a difference between the welding arc intensity and the ambient light intensity based on the first and second signals, and controlling the scale number of the light valve based on the difference.

The working method further comprises the steps of:

detecting the infrared radiation emitted by a welded object; and amplifying the detected infrared signal to obtain a third signal, determining whether the welding action is executed based on the third signal, and adjusting the sensitivity of the automatic darkening filter by adjusting the amplification factor.

With the technical solutions of the present invention, the following technical effects can be achieved.

The present invention provides an automatic darkening filter with automatic adjustment of the scale number of the light valve, and in the process of adjusting the scale number, the welding arc intensity signal is revised by acquiring the ambient light intensity to eliminate the comprehensive influence of various factors such as lighting light, sun light, and vehicle light. Moreover, the acquisition of ambient light intensity or welding arc intensity is carried out in the current working conditions, which can effectively ensure the accuracy of determination of the final scale number, and can provide the best matching scale number for different welding types, different welding currents and different welding angles, so as to achieve the best state that can satisfy the current welding.

In addition, through further optimization of the present invention, the correspondence between parameter values such as sensitivity and delay and environmental variables can be established. In this way, the adaptive adjustment of three parameters including scale number, sensitivity and delay can be achieved, thus saving the working time of users and improving the working efficiency.

DESCRIPTION OF THE DRAWINGS

In order to more clearly illustrate the embodiments of the invention or the technical solutions in the prior art, the accompanying drawings to be used in the description of the embodiments or prior art will be briefly described below. It is obvious that the accompanying drawings in the following description are only some of the embodiments recorded in the present invention, and other accompanying drawings can be obtained according to these accompanying drawings without creative work for those of ordinary skill in the art.

DETAILED DESCRIPTION

The technical solutions in the embodiments of the present invention will be described clearly and completely in conjunction with the accompanying drawings in the embodiments of the present invention. Obviously, the described embodiments are only a part of the embodiments of the present invention, rather than all the embodiments.

As shown in FIGS. 1-9, there is provided an automatic darkening filter with adaptive parameter adjustment, comprising: a welding arc intensity detection unit configured to provide a first signal for determining the welding arc intensity; a solar power supply module configured to provide electric energy for the welding arc intensity detection unit and provide a second signal for determining the ambient light intensity; and a CPU and a light valve, the CPU being configured to calculate a difference between the welding arc intensity and the ambient light intensity based on the first and second signals, and control the scale number of the light valve based on the difference.

According to the above embodiment, there is provided an automatic darkening filter with adaptive parameter adjustment, and in the process of adjusting the scale number, the welding arc intensity signal is revised by acquiring the ambient light intensity to eliminate the comprehensive influence of various factors such as lighting light, sun light, and vehicle light. Moreover, the acquisition of ambient light intensity or welding arc intensity is carried in the current working conditions, which can effectively ensure the accuracy of determination of the final scale number, and can provide the best matching scale number for different welding types, different welding currents and different welding angles, so as to achieve the best state that can satisfy the current welding. The adaptive adjustment makes it possible to save the working time of the users and improve the working efficiency.

Figure 1:
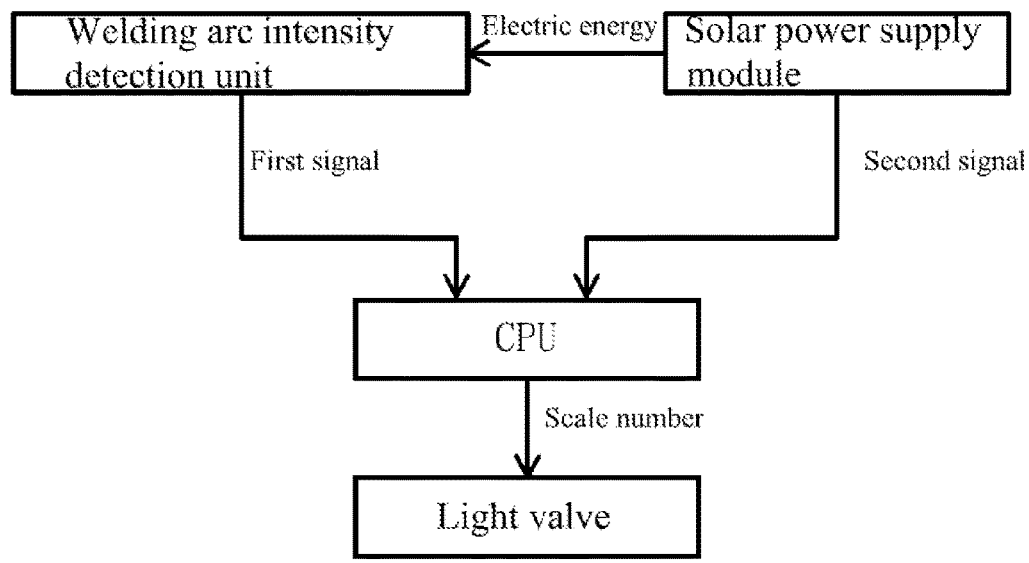
FIG. 1 is an overall block diagram of an automatic darkening filter with adaptive parameter adjustment according to the present invention.
Figure 2:
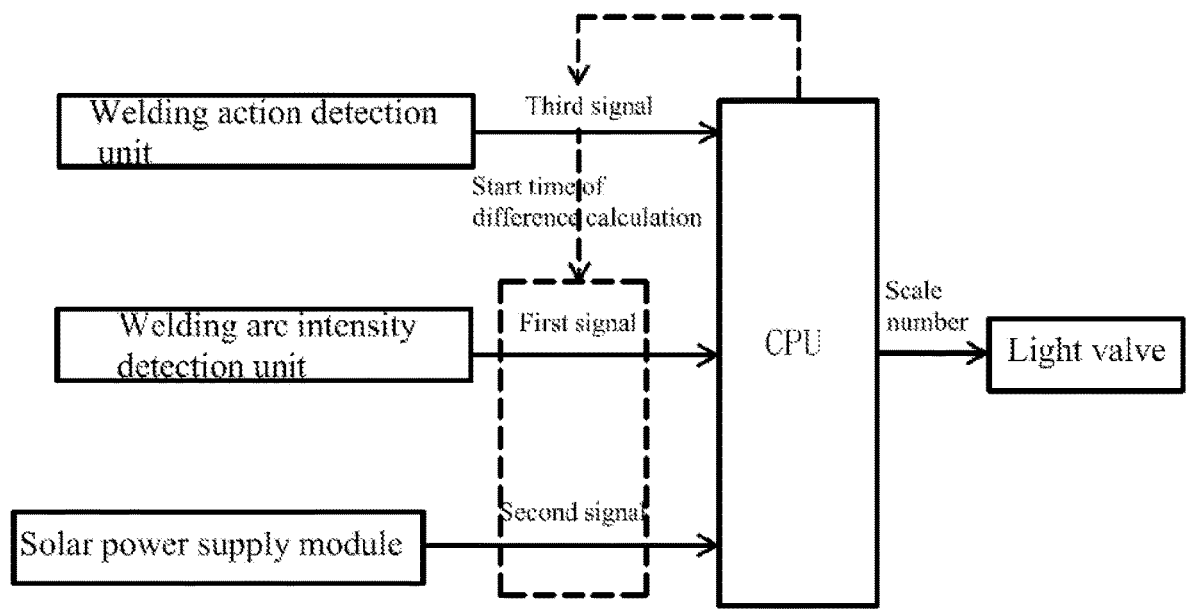
FIG. 2 is an optimized block diagram of the automatic darkening filter with adaptive parameter adjustment in FIG. 1.

For more accurate, timely and effective adjustment of the scale number, as a preferred embodiment, as shown in FIG. 2, the automatic darkening filter with adaptive parameter adjustment further comprises a welding action detection unit configured to provide a third signal for determining whether the welding action is executed, based on which third signal the CPU determines the start time of the difference calculation. The purpose of obtaining the third signal is to automatically determine the timing of controlling the light valve, which timing is determined based on the start time of difference calculation. Of course, in the process of implementation, the difference calculation is preferably carried out periodically, so that any changes in the welding work are continuously sensed by the automatic darkening filter, where the length of a single period may be set according to specific requirements. However, it is necessary to ensure the synchronization of the acquisition of the first signal and the second signal, so as to avoid the deviation of the difference caused by the time delay. When the difference calculation is not performed, it does not matter whether the first and second signals are acquired.

Figure 3:
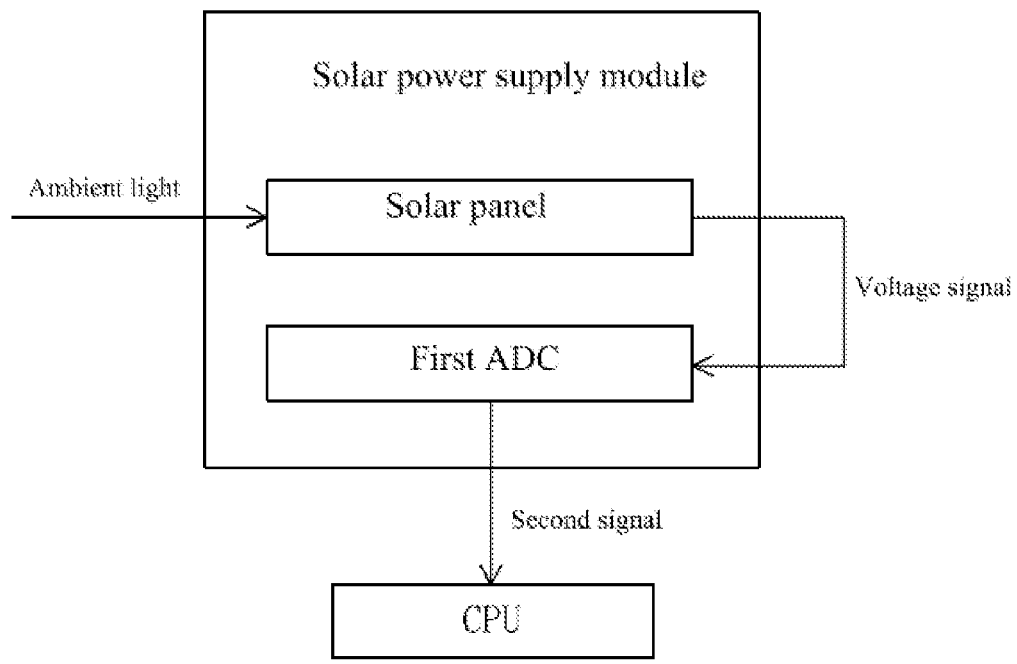
FIG. 3 is a block diagram of solar power supply module.

As shown in FIG. 3, the solar power supply module comprises: a solar panel configured to generate electricity through ambient light, and generate a varying voltage signal as the second signal based on changes in the ambient light; and a first analog-to-digital (ADC) converter configured to acquire the second signal and convert the same into a second digital signal, and transmit the second digital signal to the CPU.

In this preferred embodiment, the solar panel not only acts as a functional unit to provide electric energy and thus realize the auxiliary supply of electric energy, but also acts as a control signal provider to provide the basis for inferring the intensity of ambient light through the change of its own voltage with the ambient light, thus achieving multi-functionality. The signal is digitally converted and can be directly called by the CPU. In this preferred embodiment, the use of other types of sensors is replaced by the acquisition of voltage signals, which reduces the cost of implementation. In the process of implementation, the welding work is carried out in the local space, therefore the impact of the welding arc intensity on the solar panel voltage is negligible and has no impact on the intensity of the background light. Therefore, the accuracy of using the voltage signal as the inference basis of the ambient light is relatively high, and the high-precision calibration of the welding arc intensity can be realized.

Figure 4:
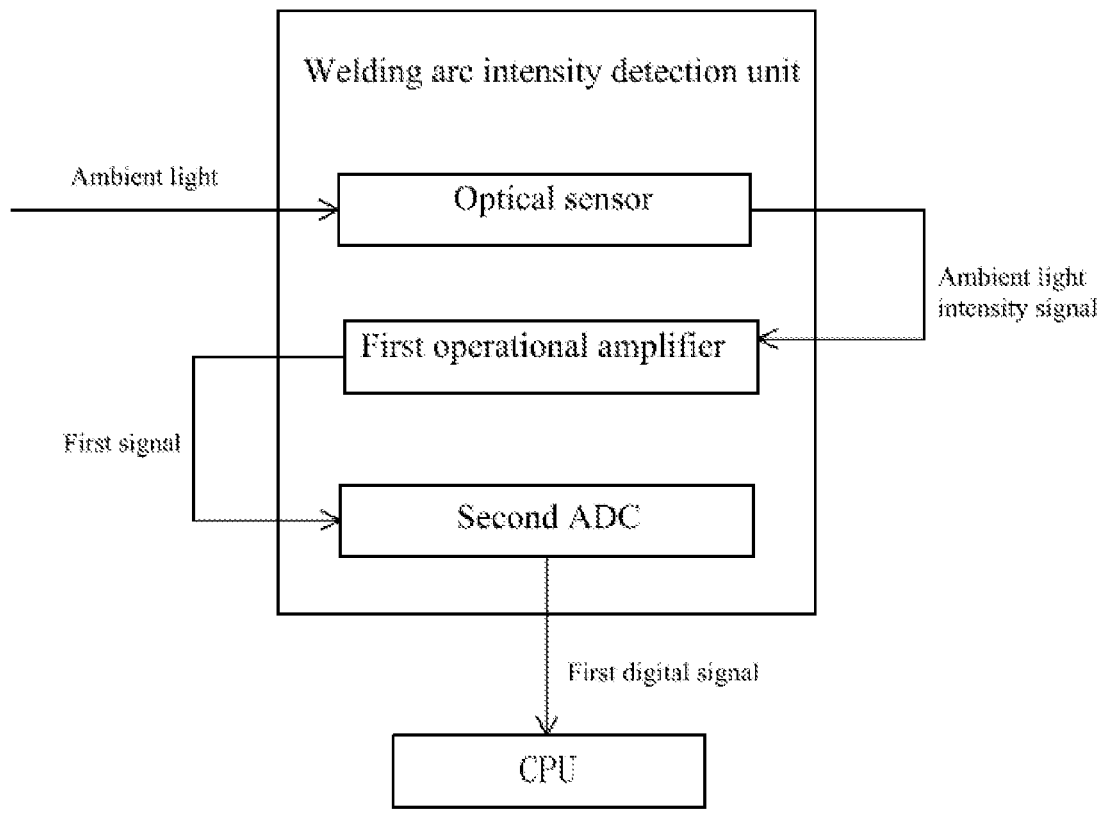
FIG. 4 is a block diagram of the welding arc intensity detection unit.

As a preferred embodiment, as shown in FIG. 4, the welding arc intensity detection unit comprises: an optical sensor configured to detect an ambient light intensity signal; a first operational amplifier configured to amplify the ambient light intensity signal as the first signal; and a second ADC converter configured to acquire the first signal and convert the same into a first digital signal, and transmit the first digital signal to the CPU. Through the use of the optical sensor, the welding actions can be acquired in time. Specifically, photodiodes with light filtering function can be used. Of course, the ambient light intensity signal acquired by the optical sensor here includes the influence of a variety of light in the environment.

Figure 5:
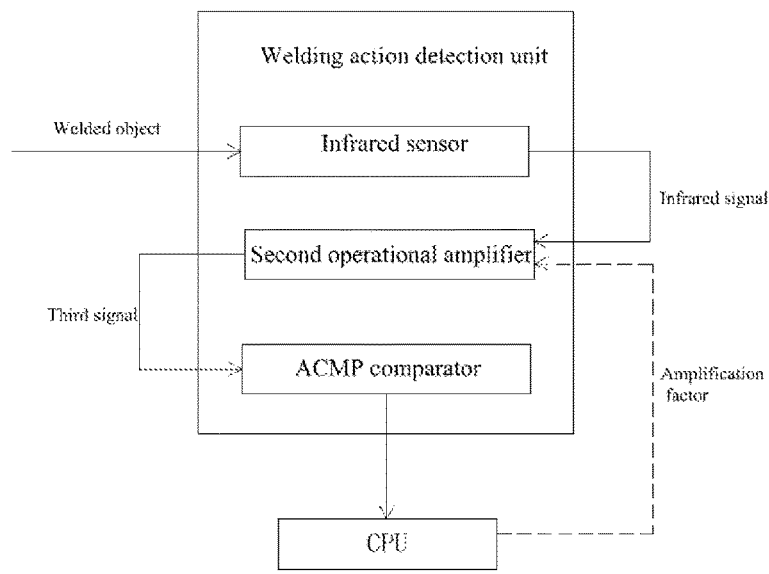
FIG. 5 is a block diagram of the welding action detection unit.

As a preferred embodiment, as shown in FIG. 5, the welding action detection unit comprises: an infrared sensor configured to detect an infrared signal radiated by a welded object; a second operational amplifier configured to amplify the infrared signal as the third signal; and an ACMP comparator configured to acquire and process the third signal, and transmit the processed signal to the CPU, so that the CPU can accurately determine the presence of an arc. Specifically, the ACMP comparator is configured to compare an input analog signal with a reference voltage, and convert the input analog signal into a digital signal output for subsequent use by the CPU. The ACMP comparator outputs a high level when the input analog signal is higher than the reference voltage, and a low level when the input analog signal is lower than the reference voltage. In this way, the irregular analog signal is made a regular digital signal, whereby the accurate determination of welding arc can be achieved. When it is determined that a welding arc is present, the light valve can be driven to blacken through the control circuit to protect the user's eyes.

To achieve automatic adjustment of the sensitivity of the automatic darkening filter, as a preferred embodiment, the CPU is coupled to the second operational amplifier to control an amplification factor of the second operational amplifier, as shown by the dotted line in FIG. 5.

By controlling the amplification factor of the second operational amplifier, different criteria for distinguishing between valid data and invalid data can be obtained. A larger amplification factor increases the proportion of valid data and thus increase the sensitivity, while a smaller amplification factor decreases the proportion of valid data and thus decrease the sensitivity. The valid data may be utilized as a third signal, while data identified as invalid due to the change in the amplification factor may be ignored, so as not to affect the operation of the welding arc intensity detection unit or solar power supply module.

When there is lighting light, sun light or other interference light in the surrounding environment, the CPU automatically reduces the amplification factor of the second operational amplifier to reduce the impact of the interference light on the automatic darkening filter and thus prevent misoperation. When the ambient light is dark and the welding arc signal is weak, the CPU automatically increases the amplification factor of the second operational amplifier to improve the detection accuracy of the welding arc signal.

Figure 6:
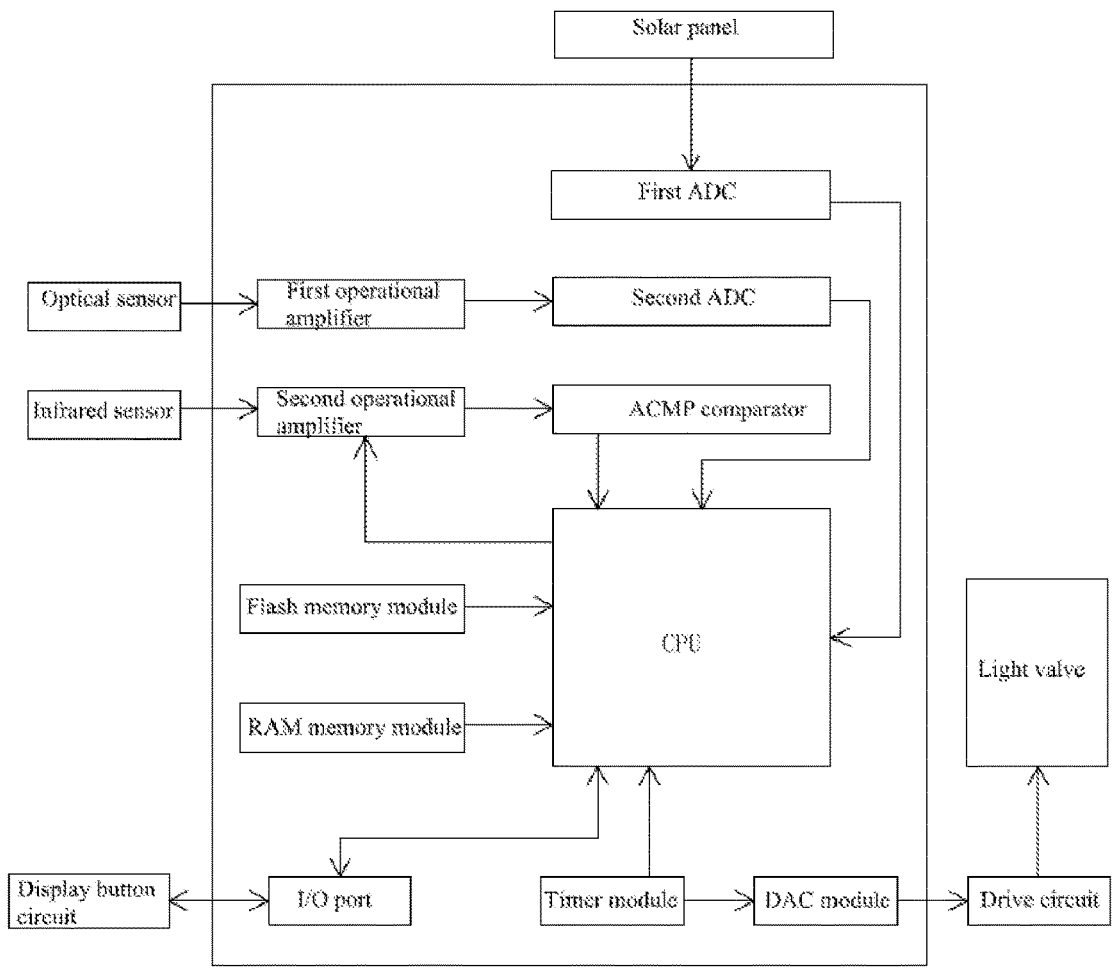
FIG. 6 is a detailed block diagram of the automatic darkening filter with adaptive parameter adjustment according to the present invention.

In the process of implementation, in order to reduce the difficulty of CPU computing, and to achieve the storage of data, as shown in FIG. 6, the automatic darkening filter with adaptive parameter adjustment comprises a RAM memory module and a Flash memory module respectively coupled to the CPU. The RAM memory module is configured to store the first digital signal and the second digital signal in a one-to-one correspondence; the Flash memory module is configured to store the correspondence between different scale numbers and different arc intensities; and the CPU is configured to obtain the arc intensity through the difference between the first digital signal and the second digital signal, and obtain the desired scale number through the correspondence.

Through the use of the two memory modules, on the one hand, the timely and effective storage of respective signals is realized, and on the other hand, it is made easier for the CPU to call the data. The required scale number can be quickly obtained by comparing the calculated difference with the prestored standard curve. The automatic scale number setting has been clearly defined in the CE regulations. The European standard EN379 specifies the calculation formula regarding the scale number and arc illuminance.

The dark state scale number $N(E_v)$ shall depend on the illuminance $E_v$, as follows:

$$N(E_v)=2.93+2.25 \log(E_v/\text{lx})$$

The following table lists the specific correspondence between some common scale numbers and ambient light intensities:

| | Dark state scale number Scale number N | | | | | | |
|---|---|---|---|---|---|---|---|
| | 8 | 9 | 10 | 11 | 12 | 13 | 14 |
| Illuminance/1x | 180 | 500 | 1400 | 3900 | 10700 | 30000 | 83000 |

Figure 7:
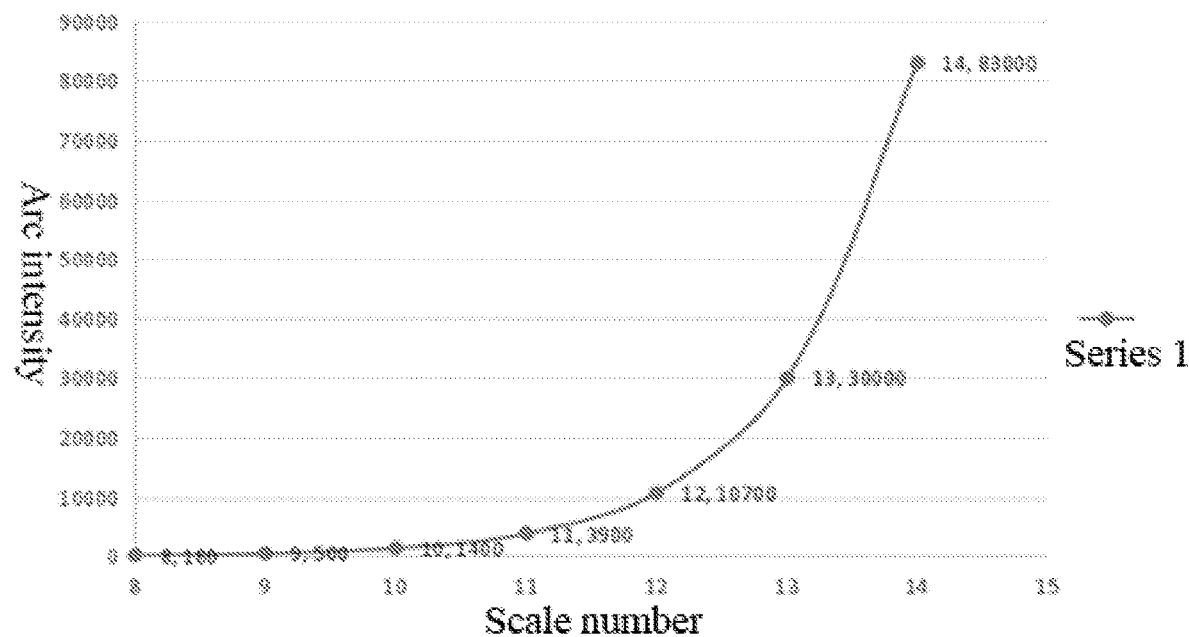
FIG. 7 shows the fitting curve of the correspondence between the scale number and the arc intensity.

In order to facilitate the CPU calculation, as shown in FIG. 7, it is preferred to fit the correspondence between the scale number and the arc intensity into a curve. Since the CPU of the microcontroller is incapable of directly processing the continuous analog signal, the continuous analog signal must be sampled using software so as to disperse the curve into an array of data to be stored in the Flash memory module.

Figure 8:
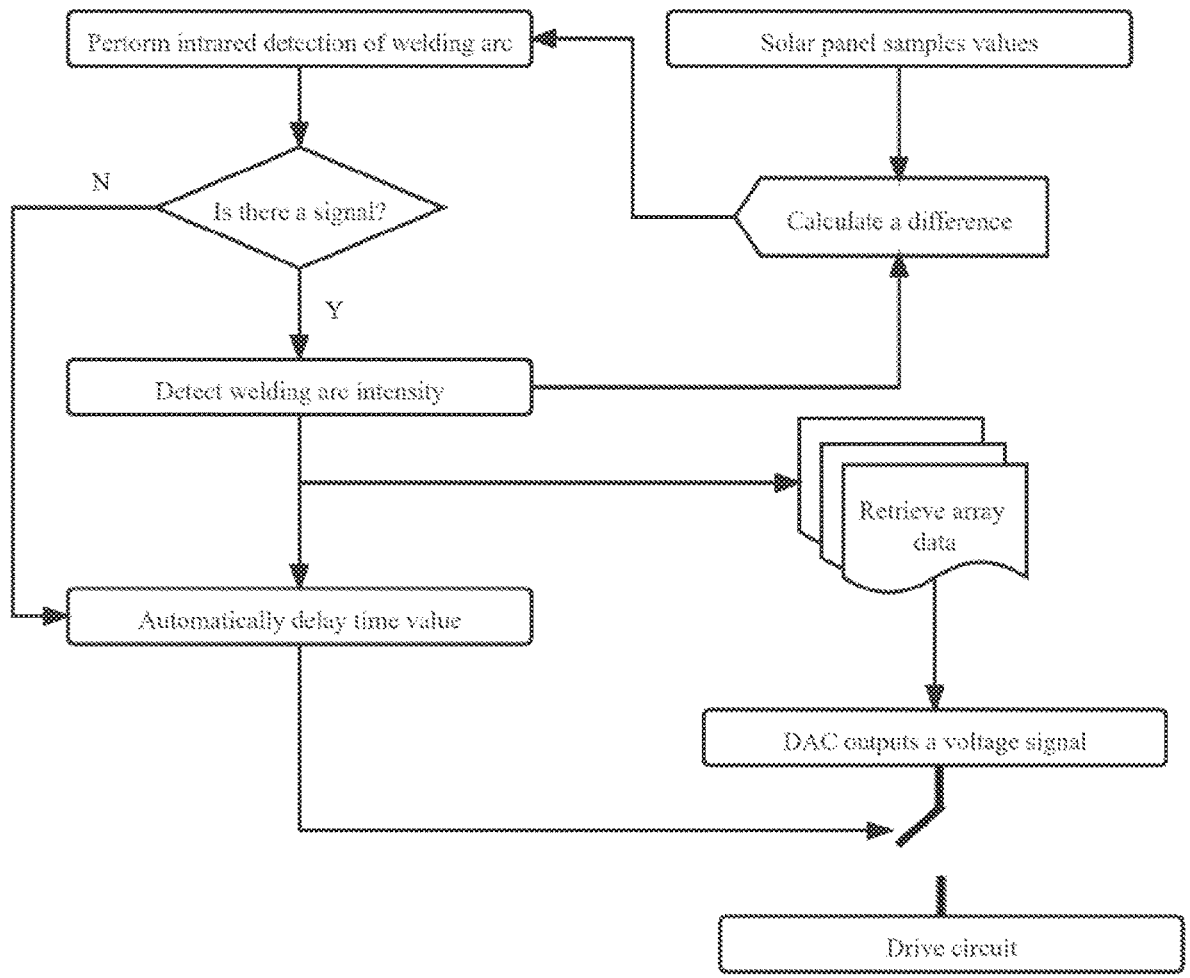
FIG. 8 is a working flow chart of the darkening filter in the automatic parameter setting mode.
Figure 9:
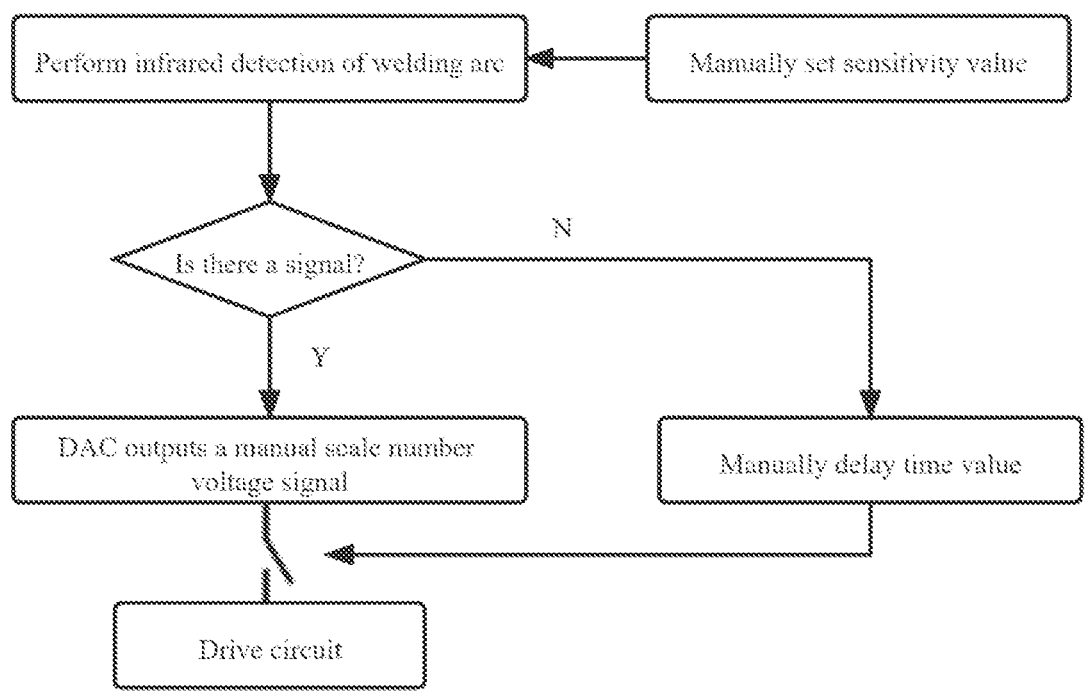
FIG. 9 is a working flow chart of the darkening filter in the manual parameter setting mode.

The light valve turns into a black state when the automatic darkening filter works. Upon disappearance of the welding arc, the workpiece burned red by welding is still hot and dazzling. In order to protect the user's eyes, the light valve will delay for a period of time and then return to the light state. Therefore, as a preferred embodiment, as shown in FIGS. 6, 8 and 9, a timer module is also provided between the CPU and the light valve. The timer module is configured to set the delay time for the light valve to change from the black state to the standby light state. When the welding arc is over, the system prepares to end the black state of the light valve and turn it into the standby light state. In the process of preparation, the infrared radiation intensity value of the welded object is continuously detected through the infrared sensor to automatically change the timing value of the internal timer module to realize the automatic delay function. The delay time can also be manually adjusted by the user, in a range of about 0.1 s to 0.9 s. It is preferred to store a delay curve in the Flash memory module in advance. The delay curve is the infrared intensity versus the corresponding delay time, which can be drawn according to the design experience value and stored in the Flash memory in the form of an array. By querying the delay curve value, the CPU can quickly determine the timing value.

In the present invention, the internal memory of the microcontroller can be used as RAM memory module and Flash memory module to store the correspondence between the scale number, sensitivity, delay time and other related parameter values and environmental variables. The respective variables are calculated by the CPU to output a corresponding scale number value through the DAC module. The delay time value is controlled by the timer module, and the amplification factor of the second operational amplifier is adjusted by the CPU so as to control the sensitivity. As shown in FIG. 8, the light valve is driven by the automatic drive circuit. Of course, the microcomputer may also detect the operation of buttons or potentiometers through the I/O port to realize the manual parameter setting mode, and then control the display of LCD display or LED indicator. The specific implementation of the manual parameter setting mode is shown in FIG. 9.

In the manual parameter setting mode, when the system detects a welding arc, the output of the DAC module is turned on, and the external power amplifier circuit drives the light valve to turn black according to the scale number value set by the user in order to protect the user's eyes. Through the sensitivity value manually set by the user, the sensitivity of the system to detect the welding arc is controlled. Through the delay time value manually set by the user, the delay time for the light valve to change from the black state to the standby light state is controlled. The user may set the relevant parameters through the operation panel to meet the current specific welding conditions. The unique full-automatic function button on the panel allows users to quickly switch between manual parameter adjustment and automatic parameter adjustment.

A working method of the automatic darkening filter with adaptive parameter adjustment comprises the steps of:

S1 of detecting the welding arc intensity to obtain a first signal for determining the welding arc intensity;

S22 of generating electricity through ambient light and using a voltage signal as a second signal for determining the ambient light intensity in the welding site; and S3 of calculating a difference between the welding arc intensity and the ambient light intensity based on the first and second signals, and controlling the scale number of the light valve based on the difference.

In the process of implementation, for a better use experience, the present invention has made optimized improvements to step S1, aiming to enable the operator to obtain a relatively soft feeling during the change of the welding arc intensity. Specifically, by adjusting the determined welding arc intensity for a short time, the adjustment of the light valve scale number caused by its change can be buffered. In other words, the change of the light valve scale number can be adjusted at least twice for each determined welding arc intensity. The final control result is achieved in a step-by-step manner, which can make the operator more comfortable to a certain extent. Of course, it should be noted that in the step-by-step process, the first-step adjustment needs to ensure that the scale number of the light valve after adjustment can ensure the operation safety of the operator, and the adjustment gradient between the respective steps needs to be controlled.

Specifically, the determined welding arc intensity is adjusted by an adjustment coefficient in at least one step within a set time, and the scale number of the light valve is controlled step by step with the adjusted welding arc intensity and the finally determined welding arc intensity respectively. When the adjustment is carried out in two steps or more, it is preferred that the adjustment ratio between the respective steps is the same. In the present invention, it is preferred that the adjustment of the light valve scale number is carried out in two steps, that is, the welding arc intensity is adjusted once, thereby reducing the control difficulty.

Firstly, the curve of welding arc intensity over time is established, and the adjustment coefficient is determined based on the curve slope at the current time point. The adjustment coefficient is used to adjust the determined welding arc intensity, where $0.9 \leq$ adjustment coefficient $\leq 1$, and decreases with the increase of the absolute value of curve slope at the current time point. When the slope is large, it indicates that the current welding arc intensity changes rapidly. The change rate between the first adjustment of the light valve scale number and the original state thereof is appropriately reduced through a relatively small adjustment coefficient, and the light valve scale number is adjusted for the first time through the adjusted welding arc intensity. When the above adjustment is complete, the influence of the adjustment coefficient is removed within the set time, and the light valve scale number is finally determined based on the actually determined welding arc intensity. The set time may be a fixed value, or it can also establish a relationship with the slope. The larger the absolute value of the slope, the smaller the value of the set time. In the process of step-by-step control, the operator's feeling comfort is adjusted as much as possible according to the degree of change of the welding arc intensity, so as to obtain short-term visual buffer on the premise of ensuring its operation safety and effectively improve the comfort of use.

The order of steps S1 and S2 can be changed, which can also achieve the technical purpose of the present invention. As described above, in this embodiment, the welding arc intensity signal is revised by acquiring the ambient light intensity to eliminate the comprehensive influence of various factors such as lighting light, sun light, and vehicle light. Moreover, the acquisition of ambient light intensity or welding arc intensity is carried in the current working conditions, which can effectively ensure the accuracy of determination of the final scale number, and can provide the best matching scale number for different welding types, different welding currents and different welding angles.

As a preferred embodiment, the working method further comprises: detecting the infrared radiation emitted by a welded object; and amplifying the detected infrared signal to obtain a third signal, determining whether the welding action is executed based on the third signal, and adjusting the sensitivity of the automatic darkening filter by adjusting the amplification factor, wherein through the detection of the welded object, more accurate and objective detection results can be obtained.

The basic principles, main features and advantages of the present invention have been shown and described above. Those skilled in the industry should understand that the present invention is not limited by the foregoing embodiments. The foregoing embodiments and descriptions only illustrate the principles of the present invention. Without departing from the spirit and scope of the present invention, the present invention will have various changes and improvements, which fall within the scope of the claimed invention. The scope of protection claimed by the present invention is defined by the appended claims and their equivalents.

The invention claimed is:

1. An automatic darkening filter with adaptive parameter adjustment, comprising:
   a welding arc intensity detection unit configured to provide a first signal for determining a welding arc intensity;
   a solar power supply module configured to provide electric energy for the welding arc intensity detection unit and provide a second signal for determining an ambient light intensity; and
   a CPU (central processing unit) and a light valve, the CPU being configured to calculate a difference between the welding arc intensity and the ambient light intensity based on the first and second signals, and control a scale number of the light valve based on the difference,
   wherein the solar power supply module comprises:
   a solar panel configured to generate electricity through the ambient light, and generate a varying voltage signal as the second signal based on changes in the ambient light; and
   a first analog-to-digital (ADC) converter configured to acquire the second signal and convert the second signal into a second digital signal, and transmit the second digital signal to the CPU.

2. The automatic darkening filter with adaptive parameter adjustment according to claim 1, further comprising a welding action detection unit configured to provide a third signal for determining whether the welding action is executed, wherein, using the third signal, the CPU determines a start time of the difference calculation.

3. The automatic darkening filter with adaptive parameter adjustment according to claim 2, wherein the welding action detection unit comprises:
   an infrared sensor configured to detect an infrared signal radiated by a welded object;
   a second operational amplifier configured to amplify the infrared signal as the third signal; and
   an ACMP (analog comparator) comparator configured to acquire and process the third signal, and transmit the processed signal to the CPU.

4. The automatic darkening filter with adaptive parameter adjustment according to claim 3, wherein the CPU is coupled to the second operational amplifier to control an amplification factor of the second operational amplifier.

5. The automatic darkening filter with adaptive parameter adjustment according to claim 3, wherein a timer module is also provided between the CPU and the light valve, which is configured to set a delay time for the light valve to change from black state to standby light state.

6. A working method of an automatic darkening filter with adaptive parameter adjustment, comprising the steps of:
   detecting a welding arc intensity to obtain a first signal for determining the welding arc intensity;
   generating electricity by a solar power supply module through an ambient light and using a voltage signal as a second signal for determining an ambient light intensity in a welding site; and
   calculating a difference between the welding arc intensity and the ambient light intensity based on the first and second signals, and controlling a scale number of a light valve based on the difference,
   wherein the solar power supply module comprises:
   a solar panel configured to generate electricity through the ambient light, and generate a varying voltage signal as the second signal based on changes in the ambient light; and
   a first analog-to-digital (ADC) converter configured to acquire the second signal and convert the second signal into a second digital signal, and transmit the second digital signal to a CPU (central processing unit).

7. The working method of the automatic darkening filter according to claim 6, further comprising the steps of:
   detecting an infrared radiation emitted by a welded object; and
   amplifying the detected infrared signal to obtain a third signal, determining whether a welding action is executed based on the third signal, and adjusting a sensitivity of the automatic darkening filter by adjusting an amplification factor of the amplified infrared signal.

* * * * *